(12) United States Patent
Dagger et al.

(10) Patent No.: US 8,729,212 B2
(45) Date of Patent: May 20, 2014

(54) POLYMER COMPOSITIONS AND DEVICES

(75) Inventors: Anthony Dagger, Heslington (GB); De Oca Horacio Montes, Heslington (GB)

(73) Assignee: Smith & Nephew, Inc., Memphis, TN (US)

( * ) Notice: Subject to any disclaimer, the term of this patent is extended or adjusted under 35 U.S.C. 154(b) by 1422 days.

(21) Appl. No.: 12/294,857

(22) PCT Filed: Mar. 23, 2007

(86) PCT No.: PCT/GB2007/001065
§ 371 (c)(1),
(2), (4) Date: Aug. 9, 2010

(87) PCT Pub. No.: WO2007/110609
PCT Pub. Date: Oct. 4, 2007

(65) Prior Publication Data
US 2010/0324605 A1    Dec. 23, 2010

(30) Foreign Application Priority Data

Mar. 27, 2006   (GB) .................................. 0606050.3

(51) Int. Cl.
*C08G 65/10* (2006.01)
*C08G 63/68* (2006.01)

(52) U.S. Cl.
USPC .................. 528/99; 90/176; 90/185; 90/194; 90/294

(58) Field of Classification Search
USPC .............................. 528/90, 99, 176, 185, 194
See application file for complete search history.

(56) References Cited

U.S. PATENT DOCUMENTS

| 4,664,972 | A |   | 5/1987 | Connolly |
|---|---|---|---|---|
| 4,731,432 | A |   | 3/1988 | Portugall |
| 4,746,721 | A |   | 5/1988 | Ueno et al. |
| 4,797,465 | A |   | 1/1989 | Portugall et al. |
| 4,814,416 | A |   | 3/1989 | Poll |
| 5,006,402 | A |   | 4/1991 | Isayev |
| 6,046,300 | A | * | 4/2000 | Umetsu et al. ................ 528/176 |

FOREIGN PATENT DOCUMENTS

| EP | 0225539 A1 | 6/1987 |
|---|---|---|
| EP | 0305683 A2 | 3/1989 |
| EP | 0226847 B1 | 8/1989 |
| EP | 0350127 A2 | 1/1990 |
| JP | 57-159816 | 10/1982 |
| JP | 60-229921 | 11/1985 |
| JP | 62-252420 | 11/1987 |
| JP | 63012630 A | 1/1988 |
| JP | 63-105026 | 5/1988 |
| JP | 2-142569 | 5/1990 |
| JP | 5025260 A | 2/1993 |

OTHER PUBLICATIONS

European Office Action issued in Application No. 07 732 127.1, mailed Apr. 30, 2009, 3 pages.
European Office Action issued in Application No. 07 732 127.1, mailed Apr. 9, 2010, 4 pages.
European Office Action issued in Application No. 07 732 127.1, mailed Nov. 19, 2010, 3 pages.
International Search Report issued in Application No. PCT/GB2007/001065, mailed Jun. 14, 2007, 3 pages.
Higashi et al., "Direct Polyesterification with Tosyl Chloride in Pyridine," Journal of Polymer Science, Polymer Chemistry Edition, vol. 23, 1985, pp. 3095-3098.
Higashi et al., "Direct Polycondensation of Aromatic Dicarboxylic Acids and Bisphenols with Tosyl Chloride and N,N-Dimethylformamide in Pyridine," Journal of Polymer Science, Polymer Chemistry Edition, vol. 22, 1984, pp. 1653-1660.
Examiner's First Report on corresponding Australian Application No. 2007231211, mailed Jan. 13, 2012, 2 pages.
Office Action; JP-2009-502194; dated Sep. 4, 2012; 16 pp.
Canadian Office Action issued Feb. 1, 2013, Application No. 2,647,415.
International Preliminary Report on Patentability issue Sep. 30, 2008, International Application No. PCT/GB2007/001065.

* cited by examiner

*Primary Examiner* — Ling Choi
*Assistant Examiner* — Gennadiy Mesh
(74) *Attorney, Agent, or Firm* — Fish & Richardson P.C.

(57) ABSTRACT

Bioresorbable or biodegradable polymers formed from the monomers including sulphonyl diphenol, hydroxybenzoic acid and dicarboxylic acid. The dicarboxylic acid can include aliphatic dicarboxylic acid or a mixture of aliphatic dicarboxylic acid and aromatic dicarboxylic acid. Between 25 and 85 molar percent of the polymer is formed from the hydroxybenzoic acid, between 7.5 and 37.5 molar percent of the polymer is formed from the sulphonyl diphenol, and between 7.5 and 37.5 molar percent of the polymer is formed from the dicarboxylic acid. Polymers can be used for manufacturing fibers and composite devices.

42 Claims, 3 Drawing Sheets

Monomers:

Polymer

POLYMER COMPOSITIONS AND DEVICES

BACKGROUND OF THE INVENTION

1. Field of the Invention

The present invention relates to polymer compositions and artefacts made therefrom. In particular the present invention relates to bioresorbable polymers having high mechanical strength and modulus and their use for the manufacture of load bearing medical devices suitable for implantation within the body.

2. Related Art

Orthopaedic surgery involves the implantation of materials that must be both biocompatible and capable of bearing high loads. Traditionally metals such as titanium and titanium alloys have been used, but these suffer a number of disadvantages. In recent years biocompatible, bioresorbable polymers have been developed that aim to overcome the deficiencies of metals in orthopaedic applications. However, current bioresorbable polymers such as poly(glycolic acid) (PGA) and poly(lactic acid) (PLA) and copolymers thereof require a great deal of processing to achieve the strength required for load-bearing orthopaedic applications. Furthermore, said materials are not stiff enough to resist deformation under high load.

SUMMARY OF THE INVENTION

According to the present invention there is provided a polymer formed from at least the following monomers: sulphonyl diphenol (BPS), hydroxybenzoic acid (HBA) and dicarboxylic acid (DCA). Polymer compositions according to the present invention are formed from at least sulphonyl diphenol, hydroxybenzoic acid and dicarboxylic acid monomers, thus the polymer compositions may also comprise other monomers. The monomers may be in their pure form or have protecting groups which are removed during the synthesis. The polymer compositions comprise sulphonyl diphenol, hydroxybenzoic acid and dicarboxylic acid. In an embodiment the polymer may be a copolyester made from the following monomers: 4,4'-sulphonyl diphenol, hydroxybenzoic acid and dicarboxylic acid.

The 4,4'-sulphonyl diphenol is aptly bisphenol-S, dimethyl bisphenol-S or tetramethyl bisphenol-S. The bisphenol may include halogens or larger alkyl groups. The hydroxybenzoic acid component may include 1,4-hydroxybenzoic acid, vanillic acid or syringic acid, although other hydroxybenzoic acids will be known to those skilled in the art. The dicarboxylic acid comprises aliphatic dicarboxylic acid, aromatic dicarboxylic acid or a mixture thereof. Suitable aliphatic dicarboxylic acids include sebacic acid, suberic acid, dodecanoic acid, adipic acid, diglycolic acid and 3,6-dioxaoctanedioic acid. Suitable aromatic dicarboxylic acids include meta-, iso- or para-arylenes which may additionally contain one or more substituents such as halogens or lower alkyl radicals. Terephthalic acid is a particularly suitable aromatic dicarboxylic acid.

In order to obtain high strength polymer it is preferable for the ratio of DCA to BPS to be close to 1 to 1. Aptly the HBA should account for between 1 and 99 molar percent of the polymer, suitably the HBA should account for between 25 and 85 molar percent of the polymer, preferably the HBA should account for between 50 and 75 molar percent of the polymer and most preferably the HBA should account for around 62.5 molar percent of the polymer.

According to the present invention there is further provided a method of manufacturing a polymer, comprising the steps of mixing sulphonyl diphenol, hydroxybenzoic acid and dicarboxylic acid in a solvent; heating the mixture to approximately 80° C.; adding Vilsmeier reagent; precipitating the resultant polymer out of the solution. In an embodiment there is provided a method for manufacturing a polymer made from the following monomers: 4,4'-sulphonyl diphenol, hydroxybenzoic acid and dicarboxylic acid. In this method the monomers are mixed in a solvent that is then heated to around 80° C. Vilsmeier reagent is then added then the polymer precipitated out of the solution.

The polymer may be further purified using methods known to those skilled in the art.

Suitable solvents include pyridine/dimethylformamides mixtures. Most ratios of pyridine to dimethylformamide work, although yields are lower when mixtures approaching pure solvents were used. There are various ways of making Vilsmeier reagent that will be known to those skilled in the art.

The resultant polymers are typically melt processable, with a melting point of less than 200° C., preferably approximately 180° C. and may show birefringence under crossed polarized light. Furthermore they are preferably capable of being injection molded and can be gamma sterilized without significant molar mass loss.

The polymers can be formed into fibres that typically have a tensile strength of at least 150 MPa and a tensile modulus of at least 3 GPa, although fibres with a tensile strength of at least 250 MPa and a tensile modulus of at least 12 GPa are preferable for certain high-strength applications. The fibres can be amorphous or semi-crystalline. A polymer comprising poly[(4-hydroxybenzoic acid)$_{50}$(vanillic acid)$_{25}$(4,4'-sulfonylbis(2-methylphenol))$_{12.5}$(dicarboxylic acid)$_{12.5}$ is particularly suitable for forming semi-crystalline fibres. The dicarboxylic acid is preferably adipic acid. The strength and tensile modulus of the fibres can be further enhanced by annealing the fibres at least 100° C.

The polymers and fibres made therefrom are bioresorbable and/or biodegradable and are therefore suitable for use in medical devices that will be used in the human body. Such devices include sutures, cables, plates, rods, screws, pins, stents, medical device coatings, drug delivery devices and composite devices or other such items. Such devices may be made by injection moulding. Injection moulded devices may have a modulus of at least 4 GPa. In another embodiment fibres are embedded within a polymer matrix to create a fibre-reinforced composite. Preferably the fibres are oriented substantially in one direction in order to improve the strength of the composite. Suitable polymer matrix materials include poly($\epsilon$-caprolactone) or other polymers known to those skilled in the art.

In an embodiment the polymer is an amorphous glass. Such glasses can be formed into an article that has shape memory properties, i.e. initially formed into an article having a first shape and subsequently plastically deformed into an article having a second shape and cooled to a temperature below the glass transition temperature of the polymer, wherein the first shape can be recovered by heating the article having the second shape above the glass transition temperature of the polymer. Polymer compositions suitable for forming into shape memory articles include poly[(4-hydroxybenzoic acid)$_{50}$(terephthalic acid)$_{12.5}$(4,4'-sulfonylbis(2-methylphenol))$_{25}$(dodecanoic acid)$_{12.5}$.

According to an embodiment of the present invention the copolyester comprises poly[(4-hydroxybenzoic acid)$_{50}$(4,4'-sulfonylbis(2-methylphenol))$_{12.5}$(adipic acid)$_{12.5}$(vanillic acid)$_{25}$].

According to an embodiment of the present invention the copolyester comprises poly[(4-hydroxybenzoic acid)$_{50}$(4,4'-sulfonylbis(2-methylphenol))$_{25}$(terephthalic acid)$_{12.5}$ (suberic acid)$_{12.5}$].

Another embodiment of the invention comprises poly[(4-hydroxybenzoic acid)$_{60}$(vanillic acid)$_{15}$(4,4'-sulfonylbis(2-methylphenol))$_{12.5}$(sebacic acid)$_{12.5}$].

Another embodiment compromises poly[(4-hydroxybenzoic acid)$_{47}$(vanillic acid)$_{23}$(4,4'-sulfonylbis(2-methylphenol))$_{15}$(sebacic acid)$_{15}$].

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

Figure 1:
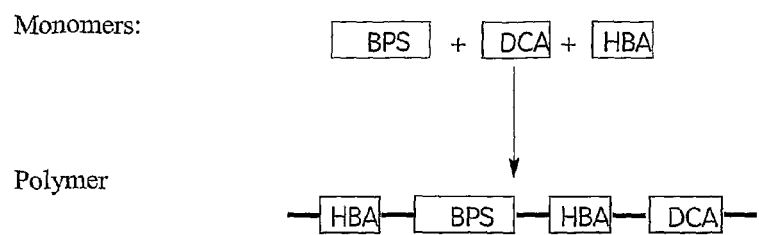
FIG. 1. shows a diagrammatic representation of the polymer

FIG. 1 shows a diagrammatic representation of the polymer where BPS is a sulphonyl linked bisphenol, DCA is an aromatic or aliphatic dicarboxylic acid or a mixture of both, and HBA is an aromatic hydroxyl acid or a mixture of such species e.g. 1,4 hydroxybenzoic acid and vanillic acid. The HBA units can occur in blocks from potentially zero up to large numbers of repeating units.

Figure 2:
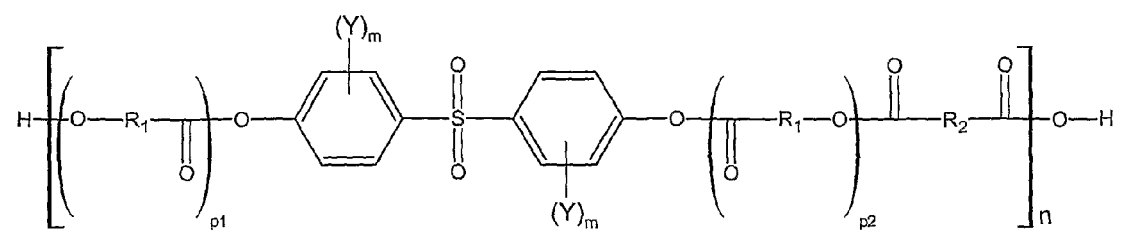
FIG. 2. shows a representation of the repeating structural unit of the polymer.

FIG. 2 shows a representation of the repeating structural unit of the polymer where Y is an inert substituent on the phenylene nucleus, for example Y is a methyl group and m=1; $R_1$ is para-substituted hydroxybenzoic acid; $R_2$ is an equimolar mixture of an aliphatic dicarboxylic acid (e.g. sebacic acid) and an aromatic dicarboxylic acid (e.g. terephthalic acid).

Figure 3:
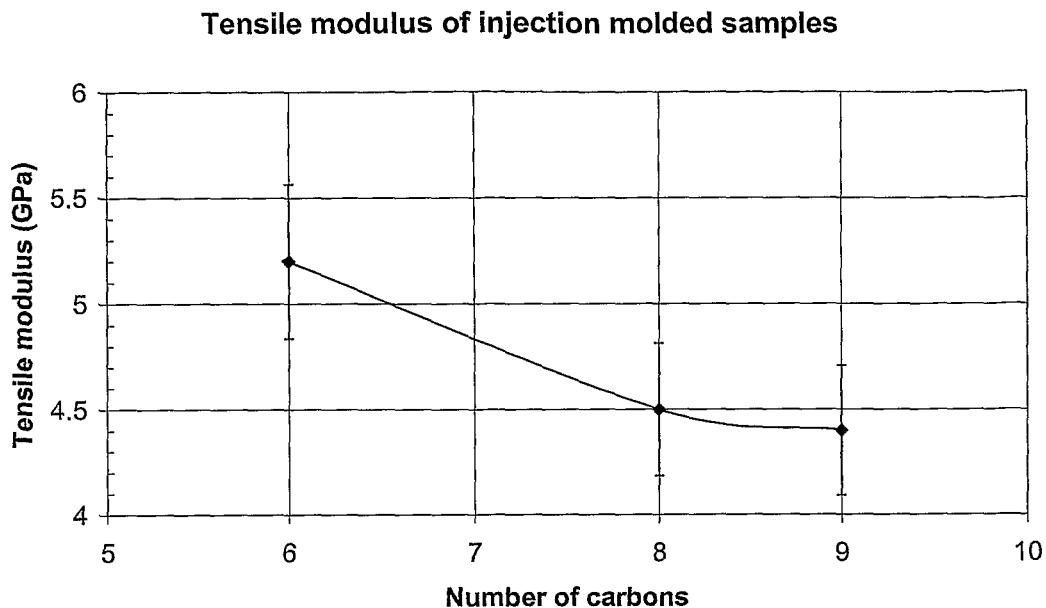
FIG. 3. shows the effect of aliphatic acid on the elastic modulus of poly[(4-hydroxybenzoic acid)$_{50}$(vanillic acid)$_{25}$(4,4'-sulfonylbis(2-methylphenol))$_{12.5}$(dicarboxylic acid)$_{12.5}$. Number of carbons of the aliphatic acid: 6 adipic acid, 8 suberic acid, 9 azelic acid.

FIG. 3 shows that increased numbers of carbons in the aliphatic group results in lower tensile modulus of the resultant polymer.

Figure 4:
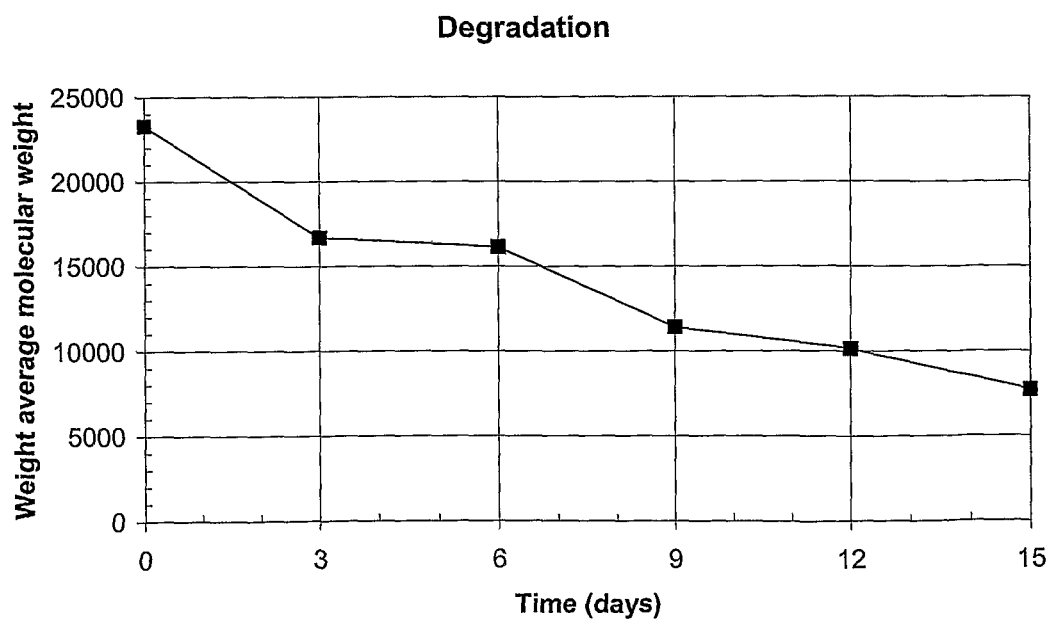
FIG. 4. shows the Degradation of poly[(4-hydroxybenzoic acid)$_{50}$(vanillic acid)$_{25}$(4,4'-sulfonylbis(2-methylphenol))$_{12.5}$(sebacic acid)$_{12.5}$ at 80° C. in simulated body fluid (phosphate buffered saline at pH 7).

FIG. 4 shows an example of polymer degradation in an aqueous environment. A polymer comprising poly[(4-hydroxybenzoic acid)$_{50}$(vanillic acid)$_{25}$(4,4'-sulfonylbis(2-methylphenol))$_{12.5}$(sebacic acid)$_{12.5}$ loses more than 50% molecular weight over a 15 day period when placed in simulated body fluid (phosphate buffered saline at pH 7) at 80° C.

Figure 5:
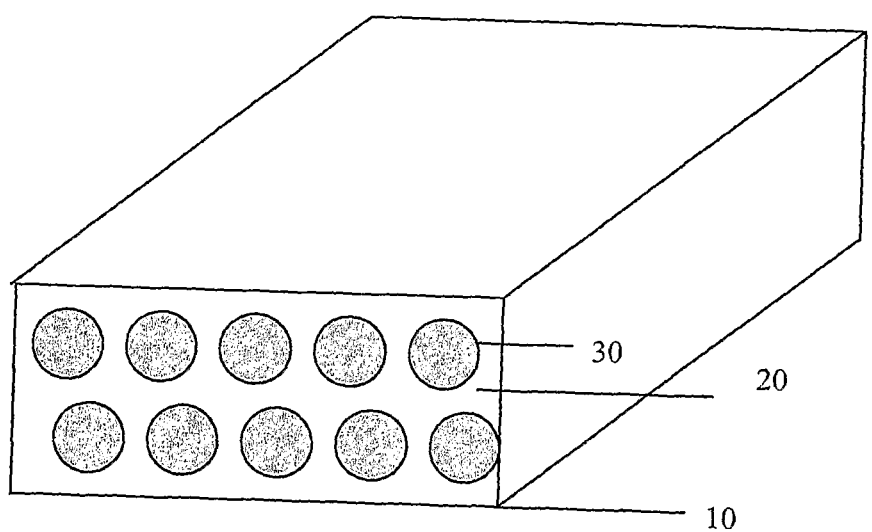
FIG. 5 shows an example of a fibre-reinforced composite made using fibres of the polymer of the present invention

FIG. 5 shows an example of a fibre reinforced composite 10. Polymer fibres 30 are embedded in polymer matrix 20 such that the polymer fibres are substantially oriented in one direction.

Example 1

2.0211 g of 4-hydroxybenzoic acid, 1.2292 g of vanillic acid, 1.0170 g of (4,4'-sulfonylbis(2-methylphenol)) and 0.7436 g of sebacic acid were dissolved in 18.75 ml of a mixed solvent of pyridine and dimethylformamide in a 2:1 ratio. A Vilsmeier reagent was prepared from 7.62 g of tosyl chloride dissolved in 9.5 ml of pyridine to which was added 4.5 ml of dimethylformamide. The Vilsmeier was added to the reagents over a period of 15 minutes at 90° C. The reaction was then precipitated into an excess of methanol and filtered off. The polymer was repeatedly dissolved and reprecipitated before being vacuum dried. Gel permeation chromatographic analysis against polystyrene standards carried out on a chloroform solution of the polymer showed it to have $M_w$ of 31345 g mol$^{-1}$, $M_n$ 8034 g mol$^{-1}$ and a polydispersity of 3.90.

Example 2

10.22 g of (4,4'-sulfonylbis(2-methylphenol)), 3.06 g of terephthalic acid, 3.22 g of suberic acid and 10.12 g of 4-hydroxybenzoic acid were dissolved in 100 ml of a mixed solvent of pyridine and dimethylformamide in a 2:1 ratio. A Vilsmeier reagent was prepared from 38.19 g of tosyl chloride dissolved in 50 ml of pyridine to which was added 22.8 ml of dimethylformamide. The Vilsmeier was added to the reagents over a period of 25 minutes at 80° C. The reaction was then precipitated into an excess of methanol and filtered off. The polymer was repeatedly dissolved and reprecipitated before being vacuum dried. 23.0 g of white powdery polymer were obtained. Gel permeation chromatographic analysis against polystyrene standards carried out on a chloroform solution of the polymer showed it to have $M_w$ of 40505 g mol$^{-1}$, $M_n$ 10012 g mol$^{-1}$ and a polydispersity of 4.05.

Example 3

10.21 g of (4,4'-sulfonylbis(2-methylphenol)), 3.08 g of terephthalic acid, 3.16 g of suberic acid and 10.43 g of 4-hydroxybenzoic acid were dissolved in 100 ml of a mixed solvent of pyridine and dimethylformamide in a 2:1 ratio. A Vilsmeier reagent was prepared from 38.65 g of tosyl chloride dissolved in 50 ml of pyridine to which was added 21.6 ml of dimethylformamide. The Vilsmeier was added to the reagents over a period of 25 minutes at 80° C. The reaction was then precipitated into an excess of methanol and filtered off. The polymer was repeatedly dissolved and reprecipitated before being vacuum dried. 22.4 g of white powdery polymer were obtained. Gel permeation chromatographic analysis against polystyrene standards carried out on a chloroform solution of the polymer showed it to have $M_w$ of 33995 g $M_n$ 6808 g mol$^{-1}$ and a polydispersity of 5.02.

Example 4

Fibers of polymer were prepared using a small ram extruder. The polymer powder was heated at 195-230° C. in a heated barrel and then hydraulically pushed through a 0.5 mm diameter die having a 60° taper. The fiber generated was hauled off as it cooled and collected on a rotating drum of diameter 12 cm rotating at 10 to 90 rpm. The fibers are useful as reinforcement in a biodegradable fiber filled composite or as a cable.

Example 5

Poly[(4-hydroxybenzoic acid)$_{50}$(vanillic acid)$_{25}$(4,4'-sulfonylbis(2-methylphenol))$_{12.5}$(adipic acid)$_{12.5}$ was annealed in a ram extruder at 280° C. for 30 minutes in order to obtain a well defined nematic melt. Highly oriented semi-crystalline fibres were prepared by ram extrusion using 4 mm diameter die at 280° C., the extruded filament was drawn from the extruded melt at 20 m/min and cooled at room temperature. Oriented semi-crystalline fibres with modulus and strength of 12 GPa and 232 MPa respectively were obtained.

Example 6

Poly[(4-hydroxybenzoic acid)$_{50}$(vanillic acid)$_{25}$(4,4'-sulfonylbis(2-methylphenol))$_{12.5}$(dicarboxylic acid)$_{12.5}$ with different aliphatic acids were injection moulded into dumbbell shape specimens at 240° C. and 840 bar. FIG. 3 shows the effect of the aliphatic acid on the elastic modulus of injection moulded bars.

Example 7

Poly[(4-hydroxybenzoic acid)$_{50}$(terephthalic acid)$_{12.5}$(4,4'-sulfonylbis(2-methylphenol))$_{25}$(dodecanoic acid)$_{12.5}$ shape memory fibres were prepared by heating the polymer up to 240° C. in order to obtain an isotropic liquid. The polymer was subsequently ram extruded at 240° C. cooling the fibres in air at room temperature. The fibres having a first shape were subsequently zone drawn at 150° C. in order to prepare oriented specimens (second shape). The oriented fibres were subsequently relaxed at 150° C., returning to the initial unoriented shape.

Example 8

Poly[(4-hydroxybenzoic acid)$_{50}$(vanillic acid)$_{25}$(4,4' sulfonylbis(2-methylphenol))$_{12.5}$(sebacic acid)$_{12.5}$ was injection moulded into rectangular bars. Samples measuring 2×8×5 mm (mass approx 0.12 g) were immersed in 5 mL of simulated body fluid (phosphate buffered saline at pH 7). Buffer and samples were contained in a sealed glass vial. Vials were placed in a fan oven at 80° C. for up to 15 days. One sample was removed at the following time points: 3,6,9,12 and 15 days. Buffers were replaced in the remaining vials to maintain pH. The sample was dried under vacuum for 24 hours at 60° C. to dry, and the weight average weight distribution was measured by GPC relative to polystyrene. FIG. 4 shows the degradation profile over the 15 day period.

Example 9

Poly[(4-hydroxybenzoic acid)$_{50}$(vanillic acid)$_{25}$(4,4'-sulfonylbis(2-methylphenol))$_{12.5}$(adipic acid)$_{12.5}$ semi-crystalline oriented fibres were embedded into a poly(ε-caprolactone) matrix and compacted at 80° C. and high pressure in order to make a unidirectional fibre reinforced composite.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A polymer formed from the monomers comprising: sulphonyl diphenol, hydroxybenzoic acid, and dicarboxylic acid,
    wherein the dicarboxylic acid comprises aliphatic dicarboxylic acid or a mixture of aliphatic dicarboxylic acid and aromatic dicarboxylic acid, between 25 and 85 molar percent of the polymer is formed from the hydroxybenzoic acid, between 7.5 and 37.5 molar percent of the polymer is formed from the sulphonyl diphenol, between 7.5 and 37.5 molar percent of the polymer is formed from the dicarboxylic acid, and the polymer is a bioresorbable or biodegradable polymer.

2. A polymer according to claim 1 that is melt processable.

3. A polymer according to claim 2 that has a melting point of approximately 180° C.

4. A polymer according to claim 1 that shows birefringence under crossed polarized microscopy.

5. A polymer according to claim 1 wherein the dicarboxylic acid comprises terephthalic acid.

6. A polymer according to claim 1 wherein the sulphonyl diphenol comprises bisphenol-S, dimethyl bisphenol-S or tetramethyl bisphenol-S.

7. A polymer according to claim 6 wherein the bisphenol comprises halogen.

8. A polymer according to claim 6 wherein the bisphenol comprises alkyl groups in the range $C_2$ to $C_{10}$.

9. A polymer according to claim 1 wherein the hydroxybenzoic acid comprises 1,4-hydroxybenzoic acid, vanillic acid or syringic acid.

10. A polymer according to claim 1 wherein the ratio of dicarboxylic acid to sulphonyl diphenol is substantially 1 to 1.

11. A polymer according to claim 1 wherein between 50 and 75 molar percent of the polymer is formed from the hydroxybenzoic acid.

12. A polymer according to claim 11 wherein 62.5 molar percent of the polymer is formed from the hydroxybenzoic acid.

13. A polymer according to claim 1 comprising poly[(4-hydroxybenzoic acid)$_{50}$(4,4'-sulfonylbis(2-methylphenol))$_{12.5}$(adipic acid)$_{12.5}$(vanillic acid)$_{25}$].

14. A polymer according to claim 1 comprising poly[(4-hydroxybenzoic acid)$_{60}$(vanillic acid)$_{15}$(4,4'-sulfonylbis(2-methylphenol))$_{12.5}$(sebacic acid)$_{12.5}$].

15. A polymer according to claim 1 comprising poly[(4-hydroxybenzoic acid)$_{47}$(vanillic acid)$_{23}$(4,4'-sulfonylbis(2-methylphenol))$_{15}$(sebacic acid)$_{15}$].

16. A polymer according to claim 1 comprising poly[(4-hydroxybenzoic acid)$_{50}$(4,4'-sulfonylbis(2-methylphenol))$_{25}$(terephthalic acid)$_{12.5}$(suberic acid)$_{12.5}$].

17. A polymer fiber comprising a polymer of claim 1.

18. A polymer fibre according to claim 17 that has a tensile strength of at least 150 MPa.

19. A polymer fibre according to claim 17 that has a tensile modulus of at least 3 GPa.

20. A polymer fibre according to claim 17 that is semi-crystalline.

21. A polymer fibre according to claim 20 comprising of poly[(4-hydroxybenzoic acid)$_{50}$(vanillic acid)$_{25}$(4,4'-sulfonylbis(2-methylphenol))$_{12.5}$(dicarboxylic acid)$_{12.5}$.

22. A polymer fibre according to claim 21 where the dicarboxylic acid is adipic acid.

23. A polymer fibre according to claim 21 that has a tensile strength of at least 250 MPa and a tensile modulus of at least 12 GPa.

24. A polymer fibre according to claim 17 that has been annealed at a temperature of at least 100° C.

25. A composite device comprising a polymer fibre according to claim 17 and a polymer matrix.

26. A composite device according to claim 25 wherein the fibres are oriented substantially in one direction.

27. A composite device according to claim 25 where the polymer matrix is poly($\epsilon$-caprolactone).

28. A polymer according to claim 1, wherein the polymer is amorphous.

29. A polymer according to claim 28 initially formed into an article having a first shape and subsequently plastically deformed into an article having a second shape and cooled to a temperature below the glass transition temperature of the polymer, wherein the first shape can be recovered by heating the article having the second shape above the glass transition temperature of the polymer.

30. A polymer according to claim 29 comprising poly[(4-hydroxybenzoic acid)$_{50}$(terephthalic acid)$_{12.5}$(4,4'-sulfonyl-bis(2-methylphenol))$_{25}$(dodecanoic acid)$_{12.5}$].

31. A device for orthopaedic repair comprising a polymer according to claim 1.

32. A device according to claim 31 wherein the device is a suture or cable.

33. A device according to claim 31 wherein the device is a plate.

34. A device according to claim 31 wherein the device is a rod.

35. A device according to claim 31 wherein the device is formed by injection molding.

36. A device according to claim 35 that has a modulus of at least 4 GPa.

37. A method of manufacturing the polymer of claim 1, comprising the steps of mixing sulphonyl diphenol, hydroxybenzoic acid and dicarboxylic acid in a solvent; heating the mixture to approximately 80° C.; adding Vilsmeier reagent; and precipitating the resultant polymer out of the solution.

38. A method according to claim 37 further comprising the step of purifying the polymer.

39. A method according to claim 37 wherein the solvent comprises pyridine and dimethylformamide.

40. The polymer according to claim 1, wherein the aliphatic dicarboxylic acid is selected from sebacic acid, suberic acid, dodecanoic acid, adipic acid, diglycolic acid, and 3,6-dioxaoctanedioic acid.

41. A polymer formed from the monomers comprising: sulphonyl diphenol, hydroxybenzoic acid, and dicarboxylic acid, wherein the dicarboxylic acid comprises aliphatic dicarboxylic acid or a mixture of aliphatic dicarboxylic acid and aromatic dicarboxylic acid, between 25 and 85 molar percent of the polymer is formed from the hydroxybenzoic acid, between 7.5 and 37.5 molar percent of the polymer is formed from the sulphonyl diphenol, between 7.5 and 37.5 molar percent of the polymer is formed from the dicarboxylic acid, and the sulphonyl diphenol comprises dimethyl bisphenol-S or tetramethyl bisphenol-S.

42. A polymer formed from the monomers consisting of: at least one sulphonyl diphenol, at least one hydroxybenzoic acid, and at least one dicarboxylic acid, wherein the dicarboxylic acid consists of aliphatic dicarboxylic acid or a mixture of aliphatic dicarboxylic acid and aromatic dicarboxylic acid, between 25 and 85 molar percent of the polymer is formed from the hydroxybenzoic acid, between 7.5 and 37.5 molar percent of the polymer is formed from the sulphonyl diphenol, and between 7.5 and 37.5 molar percent of the polymer is formed from the dicarboxylic acid.

* * * * *